(12) United States Patent
Moinard et al.

(10) Patent No.: US 10,813,801 B2
(45) Date of Patent: Oct. 27, 2020

(54) STRIP OR LAP COMPRISING LOOPS, IN THE FORM OF A LAMINATE WITH PRINTED PATTERNS

(71) Applicant: APLIX, Le Cellier (FR)

(72) Inventors: Nathalie Christine Moinard, Nantes (FR); Thierry Jacques Marche, La Chapelle Basse Mer (FR)

(73) Assignee: APLIX, Le Cellier (FR)

( * ) Notice: Subject to any disclaimer, the term of this patent is extended or adjusted under 35 U.S.C. 154(b) by 400 days.

(21) Appl. No.: 15/129,073

(22) PCT Filed: Apr. 7, 2015

(86) PCT No.: PCT/EP2015/057443
§ 371 (c)(1),
(2) Date: Sep. 26, 2016

(87) PCT Pub. No.: WO2015/155152
PCT Pub. Date: Oct. 15, 2015

(65) Prior Publication Data
US 2017/0112690 A1    Apr. 27, 2017

(30) Foreign Application Priority Data
Apr. 8, 2014 (FR) .................................. 14 00849

(51) Int. Cl.
*A61F 13/62* (2006.01)
*A61F 13/514* (2006.01)
(Continued)

(52) U.S. Cl.
CPC ........ *A61F 13/627* (2013.01); *A44B 18/0011* (2013.01); *A44B 18/0069* (2013.01);
(Continued)

(58) Field of Classification Search
CPC ............ A44B 18/0011; A44B 18/0023; A44B 18/0034; A44B 18/0069; A44B 18/008;
(Continued)

(56) References Cited

U.S. PATENT DOCUMENTS 8,092,895 B2    1/2012  Homölle et al.
2008/0102725 A1    5/2008  Lacey et al.
(Continued)

FOREIGN PATENT DOCUMENTS

EP           1781853 B1 *  2/2011  ......... A44B 18/0011
JP           2013-121428 A   6/2013
JP           2013121428 A *  6/2013  ......... A61F 13/5633

OTHER PUBLICATIONS

"JP2013121428_Machine Translation" is a machine translation of JP 2013-121428. (Year: 2013).*

*Primary Examiner* — Laura C Powers
*Assistant Examiner* — Larissa Rowe Emrich
(74) *Attorney, Agent, or Firm* — Renner Kenner Greive Bobak Taylor & Weber (57) ABSTRACT

The invention relates to a strip or lap comprising loops, in the form of a laminate with printed patterns. The laminate for forming a loop strip or lap, in particular the landing zone of nappies, includes at least one nonwoven layer having a lower face and an upper face opposite the lower face; at least one layer of ink applied to the upper face of at least the nonwoven layer; and at least one external textile layer from which loops project externally in order to engage with hooks of a self-fastening hook and loop device, at least one textile layer being secured to the upper face of at least the nonwoven layer.

20 Claims, 4 Drawing Sheets

(51) Int. Cl.
*B32B 5/02* (2006.01)
*B32B 5/26* (2006.01)
*B32B 7/12* (2006.01)
*A61F 13/84* (2006.01)
*B32B 5/14* (2006.01)
*B32B 7/08* (2019.01)
*A44B 18/00* (2006.01)

(52) U.S. Cl.
CPC .. *A61F 13/51405* (2013.01); *A61F 13/51496* (2013.01); *A61F 13/84* (2013.01); *B32B 5/022* (2013.01); *B32B 5/026* (2013.01); *B32B 5/145* (2013.01); *B32B 5/26* (2013.01); *B32B 7/08* (2013.01); *B32B 7/12* (2013.01); *A61F 2013/8497* (2013.01); *B32B 2250/03* (2013.01); *B32B 2250/04* (2013.01); *B32B 2307/4026* (2013.01); *B32B 2555/02* (2013.01)

(58) Field of Classification Search
CPC .......... A61F 13/51405; A61F 13/51496; A61F 13/581; A61F 13/627; A61F 13/84; A61F 2013/8497; A61F 13/51403–51405; A61F 13/51476–51478; B32B 5/022; B32B 5/026; B32B 5/06; B32B 5/145; B32B 5/26; B32B 7/08–12; B32B 2250/03–05; B32B 2307/4023; B32B 2307/4026; B32B 2555/02; Y10T 428/23914; Y10T 428/23957; Y10T 428/23979–23993; Y10T 428/24008; Y10T 428/24355; Y10T 428/24628–24636; Y10T 428/24802–2481; Y10T 428/24843; Y10T 428/249923
USPC ... 428/85–86, 92, 95–97, 99, 141, 174–175, 428/195.1–196, 200, 223
See application file for complete search history.

(56) References Cited

U.S. PATENT DOCUMENTS

| | | | |
|---|---|---|---|
| 2008/0227348 A1* | 9/2008 | Waller | B32B 5/26 442/59 |
| 2008/0227356 A1* | 9/2008 | Poruthoor | C09D 11/03 442/394 |
| 2008/0260989 A1* | 10/2008 | Lester | A44B 18/0011 428/100 |
| 2009/0068393 A1* | 3/2009 | Homolle | D04B 21/02 428/99 |
| 2010/0015386 A1* | 1/2010 | Baldauf | A44B 18/0011 428/99 |
| 2010/0040827 A1* | 2/2010 | Horn | A44B 18/0011 428/113 |

* cited by examiner

STRIP OR LAP COMPRISING LOOPS, IN THE FORM OF A LAMINATE WITH PRINTED PATTERNS

TECHNICAL DOMAIN

The present invention relates to a strip or lap comprising loops, in the form of a laminate, for forming the loop part of a self-fastening hook and loop device, in particular for diapers and in particular for forming a band disposed in the front part of the diaper in a central position on the belt, the band classically called the "landing zone", to enable closure of the belt of the diaper by means of the attachment with hooks emanating from legs disposed in parts of lateral ends of the rear part of the diaper. The present invention also relates to an element comprising at least one non-woven layer on an external face of which at least one layer of ink has been applied, a textile layer with loops being intended to be secured on said external face of the at least one non-woven layer.

BACKGROUND TO THE INVENTION

Already known from the prior art are strips or laps of this type in the form of a laminate comprising a non-woven textile layer forming a support on an external face of which are disposed, in succession, a layer of ink for forming patterns, for example decorative patterns, then an external textile layer in the form of a knit comprising loops intended to co-operate with hooks, the external layer in the form of a knit being secured to the support layer and/or to the layer of ink by means of a layer of adhesive. Since the knit is a low-density fabric, it allows one to see from the outside the patterns formed by the layer of ink between the knit and the non-woven support layer.

These laminates from the prior art have a number of disadvantages.

On the one hand, they are complicated to produce, and this restricts the possibility of producing them on a large scale and at low cost, features which are particularly desirable in the field of disposable diapers where production rates can exceed 1,000 diapers/min. In particular, the ink has a tendency to soil the conveying rollers of the laps, which means that they become clogged up quickly and have to be cleaned very frequently, and this clearly limits the production speed of the product. Furthermore, securing the knit in place by adhesion is made difficult by the presence of the layer of ink. On the other hand, these laminates from the prior art have an unfortunate tendency to delaminate during use, in particular if a diaper is repeatedly opened and closed.

U.S. Pat. No. 8,092,895 describes a laminate comprising a non-woven layer on which there is disposed a layer of ink and an external knit forming loops adhered to the non-woven fabric.

Furthermore, a solution is provided here to the problem of the soiling of the conveying rollers through wear by providing a pre-treatment for the upper surface of the non-woven fabric. The effect of this pre-treatment is to keep the ink above the non-woven fabric by reducing its ability to be deposited on the rollers.

This pre-treatment step involves either the use of complicated techniques or the addition of more layers intended to receive the ink.

US-A-2008/0102725 also discloses a laminate comprising an internal layer of paper on which there are patterns, and an external non-woven layer joined by hydroentanglement to the internal layer of paper. The external non-woven layer has absorptive properties for use in cleaning cloths. The production process for this laminate is complicated and the hydroentanglement for the non-woven fabric/paper connection is, furthermore, detrimental to the quality, in particular to the clarity, of the patterns.

JP-A-2013-121428 also discloses a laminate comprising a non-woven layer with loops and a non-woven support layer. Ink is applied to the non-woven fabric with loops in order to form patterns. Apart from the fact that the production technique is complicated, the patterns can not be seen well from the outside because the ink spreads diffusely in the looped non-woven fabric.

OBJECT AND SUMMARY OF THE INVENTION

The object of the invention is to overcome the disadvantages of the prior art by proposing a laminate forming a strip or lap comprising loops of a self-fastening hook and loop system, in particular for a diaper, which, while ensuring good visibility of the printed designs or patterns of the laminate, can be produced at high speed and is highly resistant to delamination during use, in particular during repeated cycles of opening and closing a diaper.

According to the invention, a laminate for forming a lap or a strip with loops, in particular the landing zone of a diaper, comprises:
  at least one non-woven layer having a lower face and an upper face opposite the lower face,
  at least one layer of ink applied to the upper face of the at least one non-woven layer; and
  at least one external textile layer from which loops project externally in order to engage with hooks of a self-fastening hook and loop device, the at least one textile layer being secured to the upper face of the at least one non-woven layer,
characterized in that the non-woven fabric and/or the ink are chosen so that the ink penetrates at least partially into the non-woven layer, the quantity of ink on the outside above the at least one non-woven layer being less than the quantity of ink on the inside of the at least one non-woven layer, in particular the quantity of ink on the outside above the at least one non-woven layer being substantially zero and substantially all of the ink being located on the inside of the at least one non-woven layer.

By thus making provision to select the non-woven fabric and/or the ink so that the ink forming the printed layer of decorative patterns is at least partially received on the inside of the non-woven layer, and is preferably substantially all received here, one clearly improves the production speed of the laminate and its resistance to delamination. In fact, since the ink is now mostly, and preferably entirely, received on the inside of the supporting non-woven fabric, it no longer interferes with the process of securing the upper textile element, for example by adhesion. Moreover, it results in the new possibility of using during this securing process a welding step, whereas in the prior art this type of process was impossible due to the presence of the layer of ink. Securing is thus simplified because it is no longer necessary to provide complex adhesives to be adapted to securing onto a layer of ink. Furthermore, the ink is no longer likely to soil the conveying rollers, thus saving the stoppage time required to clean them.

Furthermore, the securing of the upper textile element is improved, in particular by the possibility which now exists of using welding, in particular calendering, such that the laminate is less likely to delaminate, in particular as a "landing zone" for a diaper.

Preferably, all of the layer of ink is received in the at least one non-woven layer and is flush with the upper surface of the at least one non-woven layer.

According to a preferred embodiment of the invention, the securing of the at least one external textile layer with loops to the at least one non-woven layer forming a support is achieved by welding.

Preferably, this welding is achieved without the use of any substance, in particular it is achieved by thermal and/or mechanical calendering or by ultrasonic welding.

According to one embodiment of the invention, the at least one external textile layer with loops is a knit.

According to another particularly beneficial embodiment, the at least one external textile layer with loops is a non-woven fabric, in particular a consolidated and carded non-woven fabric, more particularly a calendered and carded and/or hydroentangled or similar non-woven fabric.

According to yet another beneficial embodiment, the textile layer with loops is formed by a cluster of unstrengthened fibers or filaments in a non-woven layer.

According to one embodiment, the majority, but not all, of the ink is received in the at least one non-woven layer forming a support, and the remaining minor part of the ink is received in the non-woven fabric or the cluster of fibers or filaments forming the at least one textile layer with loops so that there is no ink present between the non-woven fabric with loops and the non-woven fabric forming a support, in particular in a zone for securing the non-woven layer to the external textile layer with loops.

According to an advantageous development, means are provided for blocking the migration of ink into the at least one non-woven layer so as to keep it in the upper part of the non-woven fabric, in particular showing on the surface on the external face of the non-woven fabric, and thus ensuring good visibility of the ink from the outside or from above.

In particular, according to one advantageous embodiment, the at least one non-woven layer comprises at least two layers piled one over the other, an upper layer, from the outside, encouraging migration within it of the ink of the decorative patterns of the printed layer so as to thus receive the ink, and a lower layer, from the inside, less encouraging of the migration of this ink, and in particular a layer blocking the migration of the ink in order to form means for blocking migration of the ink.

According to one particularly beneficial embodiment, the at least one non-woven layer is formed by an upper layer of Spunbond and a lower blocking layer of the Meltblown type so as to thus form an SM (Spunbond-Meltblown) non-woven layer, the thickness of the Spunbond layer being sufficient to allow the migration of substantially all of the layer of ink within it before the latter is stopped by the Meltblown-type layer, the non-woven fabric being in particular an SMS, an SMMS, an SSMMS or the like.

According to a preferred embodiment, the laminate has no or substantially no ink on its external and internal faces when one carries out the adhesive tape test (defined below) on these two faces.

The present invention also relates to a non-woven element comprising at least one non-woven layer to an upper layer of which has been applied at least one layer of ink in the form of patterns intended to be seen from above, at least one external textile layer from which loops project externally in order to engage with hooks of a self-fastening hook and loop device, being intended to be secured to the upper face of the at least one non-woven layer so as to thus form a strip or a lap in the form of a laminate, in particular to form the "landing zone" of a diaper, characterized in that the at least one non-woven layer and/or the ink are chosen so that the ink penetrates at least partially into the non-woven layer, the quantity of ink on the outside above the at least one non-woven layer being less than the quantity of ink on the inside of the at least one non-woven layer, in particular the quantity of ink on the outside above the at least one non-woven layer being substantially zero and substantially all of the ink being located on the inside of the at least one non-woven layer.

According to one preferred embodiment, the non-woven element has no or substantially no ink on its external and internal faces when one carries out the adhesive tape test (defined below) on these two faces.

Preferably, the non-woven support layer (SMS for example) exhibits, in particular before calendering with the external textile layer with loops (carded and calendered for example), permeability to air greater than 1000 $l/m^2/s$, preferably greater than 1700 $l/m^2/s$.

The present invention also relates to a diaper incorporating a laminate according to the invention, in particular in the central part of the front part, on the belt so as to form there the "landing zone".

BRIEF DESCRIPTION OF THE DRAWINGS

As an example, preferred embodiments of the invention will now be described, referring to the drawings in which.

DETAILED DESCRIPTION OF EMBODIMENTS

In order to seal a diaper C temporarily, a hook and loop device is used. In general, the loops are disposed on the front part of the belt of the diaper, whereas the lateral legs comprising hooks project from the rear part of the belt so as to hook into the loops of the front part. However, one could provide the opposite by disposing loops in the lateral parts and hooks in the front part.

In order to make the part with loops, and in particular in the front part called the landing zone, one uses a laminate in the form of a lap comprising at least one support layer made of a non-woven fabric and an element with loops. The non-woven layer comprises an internal face intended to be on the inside, i.e. on the side of the wearer of the diaper, in particular being secured here, whereas the external layer is located on the opposite, i.e. on the outside in relation to the wearer of the diaper. This external face is intended to be covered by a textile element comprising loops.

Generally, in the present application, upper is understood to be the outside of an element and lower is understood to be the inside of an element. The outside is the side where the loops are located and by means of which the hooks hook onto the loops.

The securing of the two strata (namely the supporting non-woven fabric and the textile element with loops) of the laminate is achieved, for example, by adhesion. However, one can provide instead of this a weld, in particular by mechanical and/or thermal calendering or by ultrasound.

However, before the adhesion or the welding a layer of printing ink is applied to the external face of the non-woven fabric in order to form patterns or designs.

Figure 1:
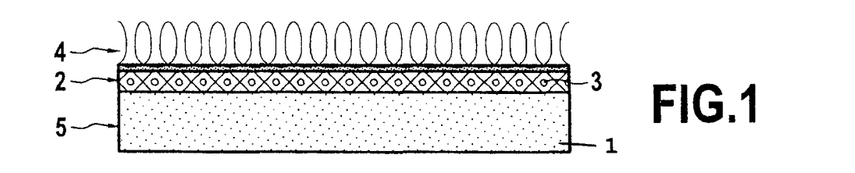
FIG. 1 is a schematic sectional view of a first embodiment of a laminate according to the invention comprising, as a textile element with loops, a knit, the connection being made by calendering.

FIG. 1 shows a first embodiment of the invention. The non-woven support layer 1 (which can, moreover, in its own right form part of the diaper) comprises an upper region 2 which is located on the outside of the support layer 1. This layer 2 is made of a material in which the ink of a printed layer 3 applied to the support layer 1 has migrated so as to be incorporated substantially entirely here, showing on the upper or external surface of the non-woven fabric 1. Thus, the layer 3 of ink no longer interferes with the process of securing a textile element that bears the loops.

In FIG. 1 this textile element with loops is formed by a knit 4 with loops. The knit 4 with loops is secured by calendaring to the external face of the non-woven fabric 1. Since all of the ink has migrated into the non-woven fabric 1, it does not interfere with the calendering process which can thus easily be implemented. Furthermore, it is no longer necessary to provide either inks or adhesives or both that are complex and expensive and which make adhesion possible despite the presence of ink.

So as to prevent the layer 3 of ink from penetrating to the bottom of the supporting non-woven fabric 1, provision is made to make the non-woven fabric in the form of a number of superimposed layers, in particular with an intermediate anti-migration layer 5 in which the ink is not able or is barely able to migrate in comparison to the upper or external layer in which it is very much able to migrate. Thus, as shown in FIG. 1, the layer of ink is stopped by the intermediate layer 5 which is made with a different structure and/or material than the upper layer 2.

In particular, one can define the capability of an ink/non-woven layer pairing to integrate the ink into the non-woven layer by the following test called the adhesive tape test:

1. A sample is selected that is formed by at least one non-woven layer to which ink has been applied. In particular, the sample can be in the form of a strip that is 10 cm long and 3 cm wide;
2. This is placed on a flat support under normal temperature and pressure conditions (25° C. and 1 atm);
3. A "Scotch" (registered trademark) type adhesive tape, for example Scotch (registered trademark) made by the company 3M, reference number 313, preferably produced less than three months ago, is placed without any pressure on a face of the sample leaving a prehension zone free;
4. Pressure is then applied, at constant speed (approximately 20 cm/s) to the whole width of the adhesive tape of the sample, and in one go, with a 2 kg application roller that is 49 mm wide so as to press the adhesive tape onto the sample
5. The adhesive tape is then pulled away so as to separate it from the sample (approximately 40 cm/s with a pulling angle of approximately 50°). This step is validated if the loops or the sample in general do not exhibit any tearing or rupture in their thickness or any defibrillation.
6. The zone of the adhesive that has been in contact with the printed zones of the sample is then visually inspected in order to assess the quantity of ink that has been transferred from the sample to the adhesive tape so as, in particular, to note the absence or the presence of ink on the adhesive tape.
7. Next, the visible surface of the ink pattern or patterns S appearing on the surface of the sample to which the adhesive tape has been applied and the visible surface S' of the pattern or patterns formed by the ink on the adhesive tape are determined, and the S'/S ratio is calculated in the form of a percentage giving a measure of the integration of the ink into the non-woven fabric, a high percentage corresponding to poor integration and a low percentage corresponding to good integration.

This test can be carried out both on the external face of the non-woven fabric or of the laminate and on its internal face opposite the non-woven fabric or the laminate.

For example, according to the invention the expression "the laminate or the non-woven element has no or substantially no ink" is understood to mean a laminate or a non-woven element for which in the present test one obtains a ratio lower than 10%, preferably lower than 5%, even more preferably less than 1%, for example less than 0.5%.

In order to calculate the visible surface areas S and S', one can in particular proceed as follows:

1. The adhesive tape including ink patterns are positioned on a sheet of paper, for example a white sheet of paper, because of the color of the supporting non-woven fabric, with dimensions of 21×29.7 mm and 80 g/m², so that the ink is captured between the sheet of paper and the adhesive tape.
2. The sample is positioned on the sheet of paper in a position next to the adhesive tape with the ink so that the patterns are aligned to the sheet of paper on the opposite side.
3. A new adhesive strip is used which is applied to the sample so that it is secured to the sheet and the patterns are totally covered with the new adhesive strip.
4. Two zones (with identical shapes and dimensions) are traced onto the sheet so that they are respectively centered on the one hand on the pattern or patterns of the adhesive tape including the ink and on the other hand on the pattern or patterns of the sample.
5. The sheet of paper is digitized (in black and white or in color) at high definition, for example 600×600 DPI (Dots Per Inch) so that the sample and the adhesive tape can be processed digitally.

6. The visible surface areas of the zone including the adhesive with the ink and the zone including the sample covered by the second adhesive strip are calculated by digital processing using specialist software, for example "ImageJ".
7. The digitized image is transformed (i.e. the zone including the adhesive tape with the ink and the zone including the sample) so that it only shows two types of pixel, a black pixel or a white pixel.
8. The number of black pixels is counted in order to determine the visible surface areas S and S'.

In the case where the user observes a lack of ink with the naked eye on the adhesive tape, it is considered that the surface area S' is zero and that all of the ink has migrated into the non-woven fabric.

For the acquisition and the processing of the image, one could also use a Cognex brand digital vision system—the "insight 7000 vision system" model—including, for example, an objective of which the focal length of the lens is 12 mm, and the dedicated "Easybuilder" (registered trademark) processing software. With this digital vision system one can, for example, count the number of black pixels so as to determine the visible surface areas S and S' after having produced a transformation similar to that of step 7 described above or else, for example, one can calculate the average at the grey level of the surface areas S and S' without the latter having been transformed according to step 7 described above. According to another method using the digital vision system cited above, one can compare the grey level of the visible surface area of the ink pattern or patterns S that appear on the surface of the sample to which the adhesive tape has been applied with grey level of the visible surface area of the ink pattern or pattern(s) S" that appear on the surface of the sample to which, one the one hand, a first adhesive strip has been applied and which has then been removed, and on the other hand to which a second adhesive strip has been added.

One thus chooses an upper layer 2 that exhibits good integration of the ink (above ratio equal to a low percentage) and an intermediate layer that exhibits poor integration (above ratio equal to a high percentage).

As can be seen in FIG. 1, since the ink 3 has stopped migrating towards the bottom of the non-woven fabric due to the intermediate blocking layer 5, one can still see the patterns well from the outside. At the same time, the layer of ink does not interfere with the securing of the knit. Furthermore, since the calendering does not involve any substance, it does not contribute to the opacity of the laminate, and in particular does not contribute to the reduction of the visibility of the printed patterns through the knit 4.

One thus obtains a laminated system that can be produced particularly quickly, which is highly resistant to delamination and which exhibits good visibility of the printed patterns.

Figure 2:
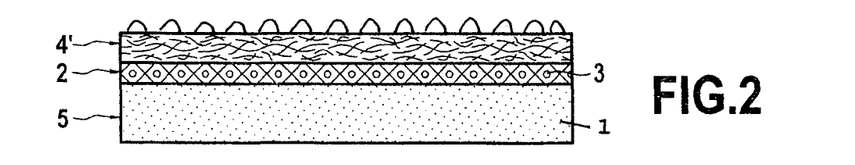
FIG. 2 is a schematic sectional view of a second embodiment of the invention in which the textile element with loops is a non-woven fabric, in particular carded and consolidated, the connection being made by calendering.

FIG. 2 shows another embodiment in which the textile element with loops is a non-woven fabric 4', preferably carded and calendered. The supporting non-woven fabric 1 is identical to that of the embodiment shown in FIG. 1. The layer 3 of ink has not entirely migrated into the supporting non-woven fabric 1. Although a majority, in particular greater than 70%, in particular greater than 90%, preferably greater than or equal to 95% of the layer of ink is located within the supporting non-woven fabric 1, some of the layer of ink has not migrated into the supporting non-woven fabric. On the other hand, this remaining part of the layer of ink has migrated into the non-woven fabric 4' so that between the non-woven fabric 4' with loops and the supporting non-woven fabric 1 there is no ink or substantially no ink present that is likely to interfere with the mutual securing process for the two non-woven fabrics. Therefore, this process can be implemented by calendering, without involving any substance, and this contributes to good visibility of the patterns defined by the layer of ink through the carded and calendered non-woven fabric 4'.

Figure 8A:
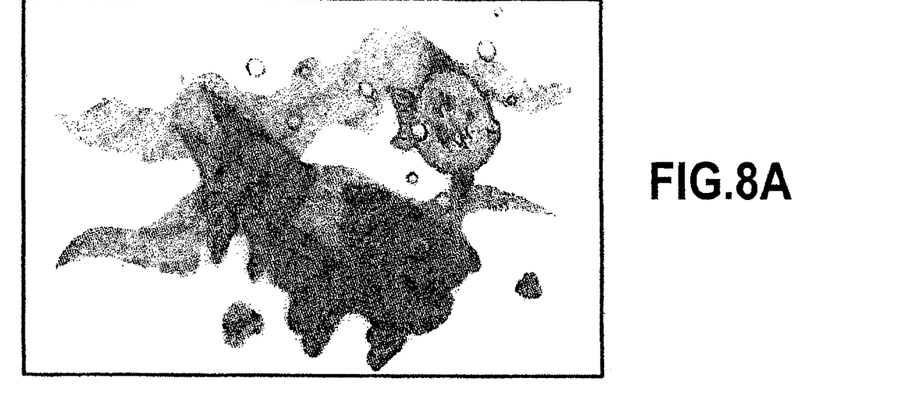
FIG. 8A is the top view (i.e. from the side of the loops or of the consolidated carded part) of a sample of a laminate comprising the printed SMS non-woven fabric of FIG. 7A and a non-woven fabric carded and calendered on the SMS.

FIG. 8A shows a sample of a laminate that corresponds to the embodiment of FIG. 2, the printed supporting non-woven fabric being made of an SMS, whereas the non-woven fabric with loops is a carded and calendered non-woven fabric.

More particularly, the layer of supporting non-woven fabric (SMS for example), before calendaring with the external textile layer with loops (carded and calendered) exhibits permeability to air greater than 1000 $l/m^2/s$, preferably greater than 1700 $l/m^2/s$ measured according to the European standard and French Textiles Standard NF EN ISO 9237 for "determining the permeability to air of materials" with a pressure indicator or a 200 Pa manometer.

More particularly, the laminate exhibits permeability to air greater than 500 $l/m^2/s$ and less than 2400 $l/m^2/s$ measured according to the European standard and the French Textiles Standard NF EN ISO 9237 for "determining the permeability to air of materials" with a pressure indicator or a 200 Pa manometer.

Figure 8B:
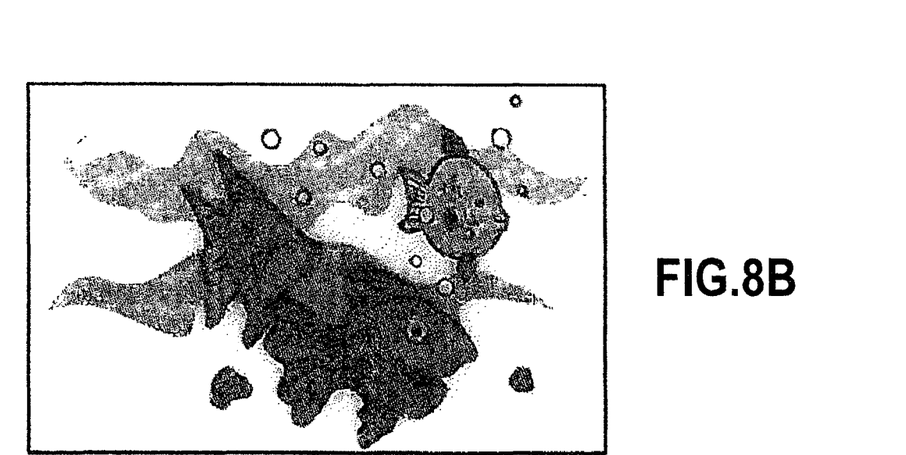
FIG. 8B is the top view of the SMS alone of the sample of FIG. 8A, after delamination of the calendered carded part.
Figure 8C:
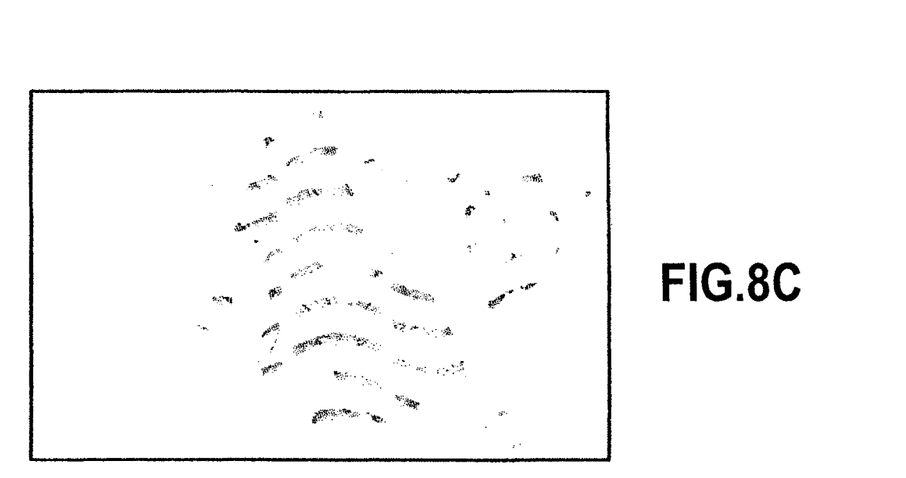
FIG. 8C is the top view of the carded part alone after it has been removed by delamination from the SMS of the sample.

Separation by hand (delamination) has taken place and one obtains on the one hand the SMS non-woven fabric shown in FIG. 8B in a top view and the carded and calendered non-woven fabric shown in FIG. 8C. As one can see in FIG. 8C, ink is present on the delaminated carded and calendered part, mainly in the old weld zones of the carded SMS non-woven fabric.

Figure 3:
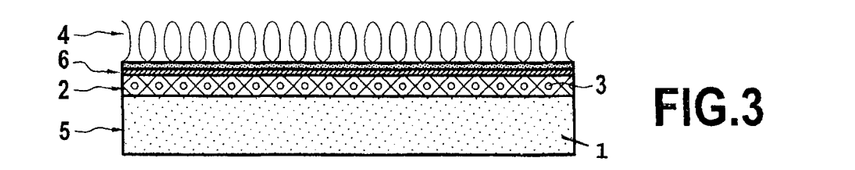
FIG. 3 is a sectional view of yet another embodiment of the invention made with a textile element with loops in the form of a knit, the connection being made by a layer of adhesive.
Figure 4:
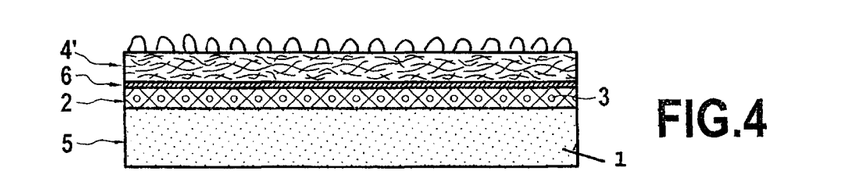
FIG. 4 is a schematic sectional view of yet another embodiment comprising, as a textile element, a non-woven fabric, in particular carded and calendered, the connection being made by a layer of adhesive.
Figure 5:
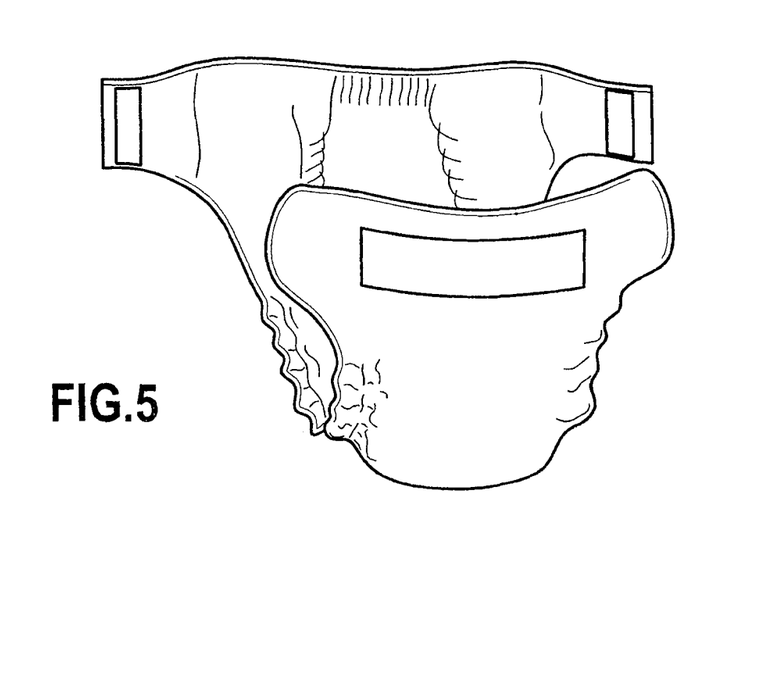
FIG. 5 shows schematically in perspective a diaper incorporating in its front part, at the centre of the belt, a laminate for forming the landing zone, this laminate being able to be any of those described in the present application as being according to the invention.

FIGS. 3 and 4 show embodiments that are respectively identical to those of FIGS. 1 and 2 in which the two support elements with loops are secured by a layer 6 of adhesive instead of by calendering.

In the present application non-woven fabric means a product obtained at the end of the formation of a strip of fibers and/or filaments which have been consolidated. The consolidation can be mechanical, chemical or thermal and is manifested by the presence of connections between the fibers and/or the filaments. This consolidation can be direct, i.e. made directly between the fibers and/or filaments by welding, or it can be indirect, i.e. by means of an intermediate layer between the fibers and/or the filaments, for example a layer of adhesive or a layer of binder. The term non-woven relates to a structure in the form of a lap or strip of fibers and/or filaments which are interlaced in a non-uniform, irregular or random manner. A non-woven fabric can have a single layer structure or a multiple layer structure. A non-woven fabric can also be joined to another material in order to form a laminate. A non-woven fabric can be made from different synthetic and/or natural materials. The natural materials are, for example, cellulose fibers such as cotton, jute, linen and the like, and can also include reprocessed cellulose fibers such as rayon or viscose. The natural fibers for a non-woven fabric can be prepared by using various processes such as carding. Synthetic materials include, but are not restricted to, for example, synthetic thermoplastic polymers which are known to form fibers that include, but are not restricted to, polyolefins, for example polyethyelene, polypropylene, polybutylene and the like; polyamide, for example polyamide 6, polyamide 6.6, polyamide 10, polyamide 12 and the like; polyesters, for example polyethylene teraphthalates, polybutylene terephthalates, polylactic acids and the like, polycarbonates, polystyrenes, thermoplastic elastomers, polymer vinyls, polyurethanes and mixtures and copolymers of the latter.

In particular, a non-woven fabric according to the definition given by the INDA (Association of Non Woven Fabrics Industry) and the EDANA (European Association of Items for Single Use and Non-Wovens) to the International Organization for Standardization (ISO) is understood to mean a sheet of fibers, continuous filaments or cut threads of any nature and/or origin which have been formed into a strip by any means and joined together by any means, with the exception of weaving and knitting. The felts obtained by a wet milling or grinding process, in particular papers, are not non-woven fabrics.

The strips obtained by a wet process, so-called "wetlaid" strips, are non-woven fabrics provided they contain a minimum of 50% fibers of synthetic origin or of non-plant origin that have a length to diameter ratio equal to or greater than 300, or a minimum of 30% synthetic fibers that have a length to diameter ratio equal to or greater than 600, and a visible maximum density of 0.40 g/cm$^3$.

In order to produce the weld between the textile element and the non-woven support, one can produce the join following patterns of any form, for example continuous, discontinuous, in a wave shape, etc. This joining pattern can be produced by using heat, pressure, ultrasound, or combinations of the latter. For example, and preferably, a non-woven fabric can be joined by passing the non-woven lap into a gap formed by a heated calender roll comprising a connection engraving and another roll so that islands of the engraving form connection zones on the non-woven lap. This description and definition of the non-woven fabric also apply to the non-woven fabric forming a support and to the non-woven fabric for the material with loops.

In order to deposit the layer of ink one can use any classical process, in particular flexography, ink jet printing, rotogravure, screen printing, heliography and the like. The printing can be in a single color or in multiple colors.

Preferably, the ink is a non-adhesive ink, i.e. an ink that is not capable of producing a sufficient connection between the textile element with loops and the supporting non-woven fabric.

An ink is made up of a mixture of three components: a coloring material, in particular a pigment or a dye; a vehicle forming the fluid phase of the ink, for example a mixture of polymers, diluents and/or solvents or else water; and additives such as dispersing or defoaming agents etc. that make it possible to optimize the characteristics of the ink.

As a mixture of polymers one can use mixtures of for example up to 50% of various acetates such as ethyl acetate, N-propyl acetate, isopropyl acetate, N-butyl acetate and mixtures thereof, up to 10% alcohol.

One can use organic pigments or minerals, for example diazoic dyes, anthraquinone, xanthene, azine dyes and the like, titanium dioxide, carbon black, iron oxides, chromium oxide and the like.

Figure 7A:
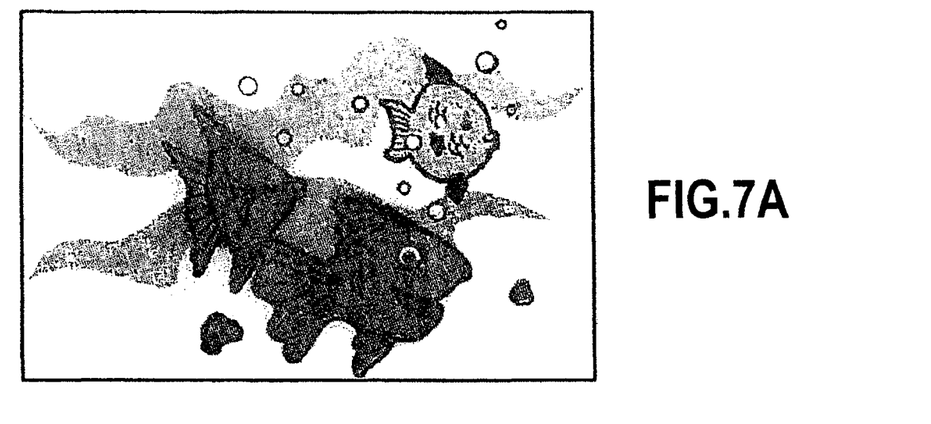
FIG. 7A is a top view of a sample of a printed SMS non-woven fabric used according to an embodiment of the invention as the non-woven layer forming a support, prior to application of the adhesive tape for said adhesive tape test.
Figure 7B:
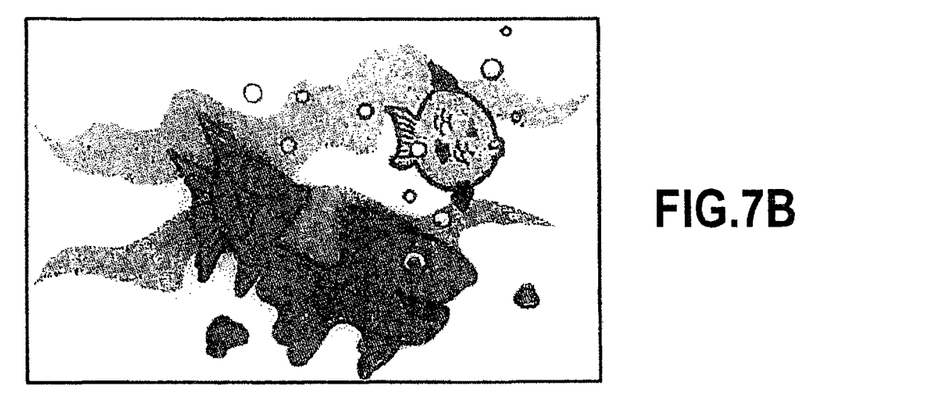
FIG. 7B is the top view of the sample of FIG. 7A after application and removal of the adhesive tape.
Figure 7C:
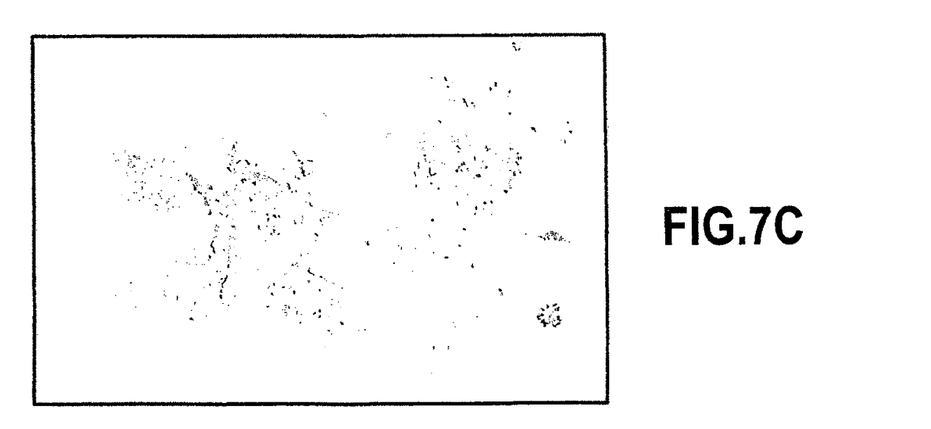
FIG. 7C is the top view of the adhesive tape after it has been applied to the sample and removed from the latter.

FIGS. 7A and 7B show top views respectively of a sample of a non-woven layer made of a printed SMS, respectively prior to application of the adhesive tape in order to carry out the adhesive tape test, and after application and removal of the adhesive tape. FIG. 7C shows the top view of the adhesive tape applied to and removed from the sample of FIG. 7A.

As can be seen in particular in FIGS. 7A to 7C, a small percentage purely of the ink has not been integrated into the SMS non-woven fabric and appears on the internal face of the adhesive tape. The ratio of the printed surface on the adhesive tape to that of the non-woven fabric is of the order of 1.5% according to the method described above.

In the following an example will be given, purely as an illustration of the invention and in a non-restrictive manner, of pairings of supporting non-woven fabric/ink or of supporting non-woven fabric/ink/non-woven fabric with loops trinomials according to the invention.

EXAMPLE

As a supporting non-woven fabric one takes an SMS with a surface density equal to 13 g/m$^2$, of which the filaments of the layers of Spunbound have an average diameter equal to 15 micrometers and the filaments of the layer of Meltblown have an average diameter of 6 micrometers, whereas the ink is made up of a mixture of a nitrocellulose resin (1%), polyacetate (12%), ethanol (47%) and pigments (5%).

The adhesive tape test is then applied and finds a printed surface ratio of 1.54%.

Figure 6:
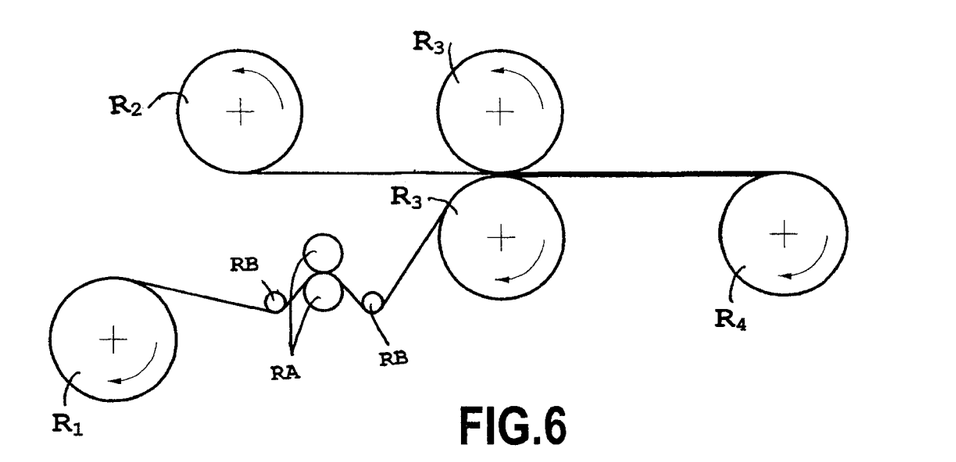
FIG. 6 is a schematic side view of an installation for the production of a laminate according to the invention, in particular for the production of a laminate according to FIG. 2.

FIG. 6 shows a basic diagram of an installation for the production of a laminate according to FIG. 2.

This installation shows in sequence both the printing of the SMS and the calendering of the calendered carded part on the printed SMS. In one embodiment one could envisage separating the two production steps.

According to the example shown in FIG. 6, the roll R1 is arranged so as to unroll the unprinted SMS so that it is printed by the rolls RB, the function of the rolls RA being to bring tension into the SMS. The ink of the printed SMS is then dried, in particular at least part of the vehicle forming the fluid phase of the ink is evaporated by adapted means that are not shown.

The roll R2 is arranged so as to unroll the calendered carded fabric so that the calendered carded fabric and the printed SMS are joined by thermal calendaring by the rolls R3 (one of which comprises engraving) so as to form the laminate according to the invention. The roll R4 is arranged to roll up the laminate that has been obtained.

According to the present invention loop means a filament and/or a fiber that comprises two ends, each one joined to the support at a respective point of the support or at a same point of the support. A loop can also be formed from a number of filaments or fibers that are joined to one another and of which at least two are joined to the support at one point or at two respective distinct points.

Non-woven fabric with loops means a non-woven fabric that makes loops after being joined to the support.

In general, the fibers and the filaments differ mainly by their length and by their production method.

Filaments mean the unitary elements, with very great lengths with respect to the diameter to which their section is assigned, extruded continuously in order to directly form a strip of non-woven fabric that can then be consolidated by thermo-linking or any other means so as to make it possible to achieve the desired performance and/or their transportation. Preferably the filaments exhibit a length greater than 120 mm.

Fiber is understood to be the generic term designating a textile material or a textile material element with reduced length less than the length of the filaments and able to be spun and/or used in the production of non-woven fabrics. A distinction can be made between two types of fiber—the short fibers formed discontinuously with a small length of less than 70 mm (preferably 25 mm to 60 mm) and the long fibers formed discontinuously with a large length of greater than 70 mm (preferably 80 mm to 120 mm).

Unlike filaments that are consolidated directly after having been extruded, fibers are aligned and organized in a strip during a carding step that is well known to the person skilled in the art. This strip can then be consolidated by thermal linking or by any other means so as to make it possible to achieve the desired performance and/or their transportation.

The invention claimed is:

1. A laminate for forming a lap or a strip with loops comprising:
   at least one non-woven layer (1) having a lower face and an upper face opposite the lower face,
   at least one layer (3) of ink applied to the at least one non-woven layer; and
   at least one external textile layer (4) from which loops project externally in order to engage with hooks of a self-fastening hook and loop device, the at least one textile layer being secured to the upper face of the at least one non-woven layer,
   characterized in that the at least one non-woven layer (1) and/or the ink (3) are chosen so that the ink penetrates at least partially into the at least one non-woven layer, the quantity of ink on the at least one non-woven layer being less than the quantity of ink inside the at least one non-woven layer, wherein the ink is present in an uppermost part of said at least one non-woven layer (1) starting from the upper face thereof.

2. The laminate according to claim 1, characterized in that all of the layer of Ink (3) is inside the at least one non-woven layer and is flush with the upper surface of the at least one non-woven layer (1).

3. The laminate according to claim 1, characterized in that the securing of the at least one external textile layer (4) with loops to the at least one non-woven layer (1) is achieved by welding.

4. The laminate according to claim 3, characterized in that this welding is achieved without the use of any substance.

5. The laminate according to claim 1, characterized in that the at least one external textile layer with loops is a knit.

6. The laminate according to claim 1, characterized in that the at least one external textile layer with loops is a non-woven fabric.

7. The laminate according to claim 1, characterized in that the at least one textile layer with loops is formed by a duster of unstrengthened fibers or filaments.

8. The laminate according to claim 6, characterized in that the majority, but not all, of the ink is received in the at least one non-woven layer, and the remaining minor part of the ink is received in the non-woven fabric or the duster of fibers or filaments forming the at least one textile layer with loops.

9. The laminate according to claim 1, characterized in that means (5) are provided for blocking the migration of ink into the at least one non-woven layer so as to keep the ink in an upper part of the at least one non-woven layer.

10. The laminate according to claim 1, characterized in that the at least one non-woven layer comprises at least two layers piled one over the other, an upper layer, encouraging migration within the upper layer of the ink of decorative patterns of the printed layer so as to thus receive the ink, and a lower layer, less encouraging of the migration of this ink.

11. The laminate according to claim 10, characterized in that said upper layer is a Spunbond layer and said lower layer is of a Meltblown type so as to thus form an SM (Spunbond-Meltblown) non-woven fabric, the thickness of the Spunbond layer being sufficient to allow the migration of substantially all of the layer of ink within Spunbound layer before ink is stopped by the Meltblown-type layer.

12. A non-woven element comprising at least one non-woven layer to which has been applied at least one layer of ink in the form of patterns intended to be seen from above, at least one external textile layer from which loops project externally in order to engage with hooks of a self-fastening hook and loop device, being intended to be secured to an upper face of the at least one non-woven layer so as to thus form a strip or a lap in the form of a laminate, characterized in that the at least one non-woven layer and/or the ink are chosen so that the ink penetrates at least partially into the non-woven layer, the quantity of ink on the upper face of the at least one non-woven layer being less than the quantity of ink on the inside of the at least one non-woven layer, wherein the ink is present in an uppermost part of said at least one non-woven layer starting from the upper face thereof.

13. The element according to claim 12, characterized in that the non-woven element extends between an external face and an internal face and there is no or substantially no ink on said external and internal faces when one carries out an adhesive tape test on these two faces.

14. The element according to claim 12, characterized in that the at least one non-woven layer exhibits permeability to air greater than 1000 $l/m^2/s$.

15. A diaper comprising a laminate according to claim 1.

16. The laminate according to claim 4, characterized in that welding is achieved by a method selected from the group consisting of thermal calendering, mechanical calendering, and ultrasonic welding.

17. The laminate according to claim 6, characterized in that the at least one external textile layer with loops is a consolidated and carded non-woven fabric.

18. The laminate according to claim 10, characterized in that said lower layer encouraging less of the migration of this Ink is a layer blocking the migration of the ink in order to form a means for blocking migration of the ink.

19. The laminate according to claim 11, characterized in that the at least one non-woven layer is selected from the group consisting of an SMS, an SMMS, and an SSMMS.

20. A non-woven element according to claim 12 and forming a landing zone of a diaper.

* * * * *

UNITED STATES PATENT AND TRADEMARK OFFICE
CERTIFICATE OF CORRECTION

PATENT NO. : 10,813,801 B2  
APPLICATION NO. : 15/129073  
DATED : October 27, 2020  
INVENTOR(S) : Nathalie Christine Moinard and Thierry Jacques Marche

Page 1 of 1

It is certified that error appears in the above-identified patent and that said Letters Patent is hereby corrected as shown below:

In the Claims

In Column 11, Line 48 (Claim 8, Line 4) the word "duster" should read --cluster--.

Signed and Sealed this  
Twenty-second Day of December, 2020

Andrei Iancu  
*Director of the United States Patent and Trademark Office*